(12) United States Patent
Hsu et al.

(10) Patent No.: US 8,927,499 B2
(45) Date of Patent: Jan. 6, 2015

(54) GLYCINE DERIVATIVE CAPABLE OF INHIBITING MELANIN FORMATION AND COMPOSITION USING THE SAME

(71) Applicant: Corum Inc., Taipei (TW)

(72) Inventors: Nai-Hsuan Hsu, Taipei (TW); Chiao-Yi Hsu, Taipei (TW); Ssu-Ching Wang, Taipei (TW); Ting-Wan Chen, Taipei (TW); Chu-Yi Pang, Taipei (TW)

(73) Assignee: Corum Inc., Taipei (TW)

( * ) Notice: Subject to any disclaimer, the term of this patent is extended or adjusted under 35 U.S.C. 154(b) by 0 days.

(21) Appl. No.: 14/159,741

(22) Filed: Jan. 21, 2014

(65) Prior Publication Data

US 2014/0134121 A1    May 15, 2014

Related U.S. Application Data

(63) Continuation of application No. 13/128,446, filed as application No. PCT/CN2010/001665 on Oct. 22, 2010, now abandoned.

(51) Int. Cl.
| | |
|---|---|
| *A61P 17/00* | (2006.01) |
| *C07C 233/47* | (2006.01) |
| *A61K 8/44* | (2006.01) |
| *A61Q 19/02* | (2006.01) |
| *C07C 237/22* | (2006.01) |
| *A61Q 19/08* | (2006.01) |

(52) U.S. Cl.
CPC .............. *C07C 233/47* (2013.01); *A61K 8/44* (2013.01); *A61Q 19/02* (2013.01); *C07C 237/22* (2013.01); *A61Q 19/08* (2013.01)
USPC ........................................ 514/18.8; 514/21.91

(58) Field of Classification Search
None
See application file for complete search history.

(56) References Cited

U.S. PATENT DOCUMENTS

2005/0180953 A1*    8/2005    Nebolsin et al. ............. 424/85.4

* cited by examiner

*Primary Examiner* — Maury Audet
*Assistant Examiner* — Fred Reynolds
(74) *Attorney, Agent, or Firm* — WPAT, PC; Justin King

(57) ABSTRACT

The invention provides a method for inhibiting melanin formation composition by applying a glycine derivative, having a structure shown in the following general equation (I):

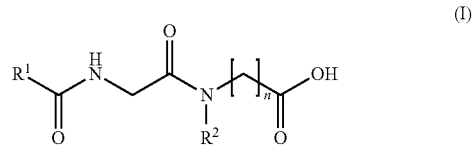

wherein $R^1$ represents a C1~C4 alkyl group; $R^2$ represents a hydrogen atom or a methyl group; and n represents an integer of 1~6.

7 Claims, No Drawings

GLYCINE DERIVATIVE CAPABLE OF INHIBITING MELANIN FORMATION AND COMPOSITION USING THE SAME

CROSS-REFERENCE TO RELATED APPLICATION

This application is a continuing application of and claims priority benefit of application Ser. No. 13/128,446, filed on May 10, 2011, now pending, which is based upon and claims the benefit of priority from China application Ser. No. PCT/2010/001665, filed on Oct. 10, 2010, the entirety of the above-mentioned patent application is incorporated herein by reference and made a part of this specification.

BACKGROUND OF THE INVENTION

1. Field of the Invention

The present invention is generally related to a glycine derivative, and more particularly to a glycine derivative capable of inhibiting melanin formation and composition using the same.

2. Description of the Prior Art

In general, melanin formation is considered to be related to tyrosinase. Tyrosine naturally exists in epidermal cells and is the precursor or melanin. Melanin formation comprises the following steps tyrosine→Dopa→Dopaquinone→Dopachrome→melanin, melanin is formed and tyrosinase is an important enzyme in the melanin formation process. The hydroxylase activity of tyrosinase catalyzes the reaction of converting tyrosine into dopa and the oxidase activity of tyrosinase catalyzes the reaction of converting dopa into dopaquinone. As long as a substance can effectively act on epidermal cells to inhibit melanogenesis or inhibit the formation of any product in the sequence of melanin formation, the substance can be used as an effective ingredient for skin whitening. The first step to initiate melanin formation is that tyrosinase catalyzes the reaction of converting tyrosine into dopa and thus the whole sequence of melanin formation can be inhibited by inhibiting the activity of tyrosinase. The tyrosinase inhibitor is one of the effective ingredients for skin whitening.

However, the mechanisms of inhibiting melanin formation of various effective skin whitening ingredients are not all the same and also are not completely realized. The well-known skin whitening ingredients, such as Kojic acid, ascorbic acid derivatives, arbutins, etc., are compounds capable of inhibiting the activity of tyrosinase.

Kojic acid is not stable in a solution to make formulation manufacturing process complicate (referring to U.S. Pat. No. 6,306,376) and may cause skin allergy (referring to Contact Dermatitis, January 1995, Vol. 42(1), Page 9~13) while applied as a skin care product. The above mentioned problems both restrict the applicability of skin whitening formulation thereof.

Ascorbic acid is very unstable and can be easily oxidized and deteriorated. Thus, usually an ascorbic acid derivative is used instead to improve the stability of formulation. However, in the formulation, stabilizer like sodium hydrogen sulfite is added or a buffer solution is used to reduce the level of oxidation or color change (referring to embodiments of U.S. Pat. No. 6,801,050). However, using sulfite as a stabilizer causes the resulting product having an irritating smell problem (referring to U.S. Pat. No. 6,020,367). Therefore, such a method cannot solve both the color and smell problems in the whitening formulation.

Although arbutin has whitening effect, the structure of arbutin is glycosylated hydroquinone and the formulation containing arbutin may have color change due to oxidation of aromatic phenol moiety to cause the difficulty in formulation manufacturing. Besides, the water solubility of arbutin is low to result in low concentration in the formulation so that the resulting whitening effect is low in practice (referring to Japan patent application No. 2009-67691). Japan patent application No. 2009-67691 discloses whitening cosmetics containing nano arbutin but it has problems of being very difficult to produce, inconvenient in use, and difficulty in being absorbed by skin.

U.S. Pat. No. 6,365,135 discloses use of amino phenol amide derivatives as depigmentation agents. Besides, Japan patent application No. H07-061905 and H07-233022 also disclose amino phenol amide derivatives as whitening ingredients. In the reports, it is suggested that tyrosinase is copper-containing polyphenol oxidase and a compound containing phenol structure(s) may be an effective ingredient to inhibit the activity of tyrosinase because of the structural similarity with tyrosinase. However, the structure of amino phenol amide derivatives comprises aromatic phenol moieties and derivatives thereof that are easy to be oxidized.

Japan patent application No. H05-032533, H06-345797, and H05-170637 disclose various dipeptides having whitening effect. In these prior arts, the amino acid side chains in dipeptides all comprise thiol groups and derivatives thereof, aromatic groups or aromatic phenol groups and derivatives thereof. The melanin inhibition mechanisms of the disclosed dipeptides are not clear. For example, the tyrosinase inhibiting rates of dipeptides disclosed in table 1 of Japan patent application No. H05-170637 are in the range of 3%~56%. Therefore, not all dipeptides are good whitening ingredients.

However, in practice, when manufacturing and applying the whitening skin care formulation, except the effectiveness of the major ingredients, the stability in the formulation should also be considered at the same time to avoid generating cross reaction with solvents and other additives in the formulation to cause formulation deterioration to generate color and smell problems. In view of the above problems, it is necessary to develop a novel whitening ingredient suitable for various whitening care products, such as cream, emulsion, gel, lotion, etc., and having stability in a formulation to fulfill the industrial needs.

SUMMARY OF THE INVENTION

In light of the above background, in order to fulfill the requirements of the industry, a glycine derivative capable of inhibiting melanin formation is provided. The glycine derivative can be used as a skin whitening ingredient and can be applied in various whitening compositions.

Furthermore, one object of the present invention is to provide a glycine derivative that does not comprise an aromatic group, aromatic phenol and derivative thereof, thiol group and derivative thereof and has no optical activity. The glycine derivative of the invention comprises a structure having oxidative stability and single bioactivity. Besides, the glycine derivative of the invention has excellent color stability.

One embodiment of the invention is to provide a glycine derivative, having a structure shown in the following general equation (I):

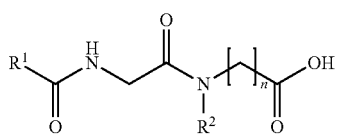
(I)

wherein $R^1$ represents a C1~C4 alkyl group; $R^2$ represents a hydrogen atom or a methyl group; and n represents an integer of 1~6.

In one embodiment, the glycine derivative is 3(2-acetylamino-acetylamino)-propionic acid having a structure shown in the following general equation (II):

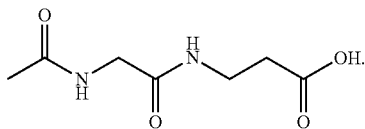
(II)

In one embodiment, the glycine derivative is 4-(2-Acetylamino-acetylamino)-butyric acid having a structure shown in the following general equation (III):

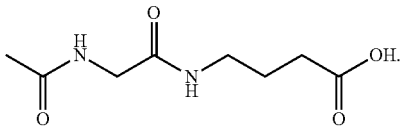
(III)

In one embodiment, the glycine derivative is [(2-Acetylamino-acetyl)-methyl-amino]acetic acid having a structure shown in the following general equation (IV):

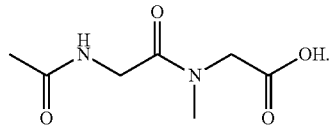
(IV)

In one embodiment, a solution or a buffer solution containing the glycine derivative with addition amount of 0.05~10 wt % (weight ratio) has light transmittance more than or equal to 97% in the wavelength range of 420~500 nm. In one embodiment, the buffer solution comprises citric acid and salts thereof. The solution or the buffer solution containing the glycine derivative with addition amount of 0.05~10 wt % (weight ratio) has light transmittance more than or equal to 98% at the specific wavelength 440 nm.

Another embodiment of the invention is to provide a whitening composition, comprising: a glycine derivative with addition amount of 0.05~10 wt % (weight ratio) wherein the glycine derivative has a function of inhibiting melanin formation and has a structure shown in the following general equation (I):

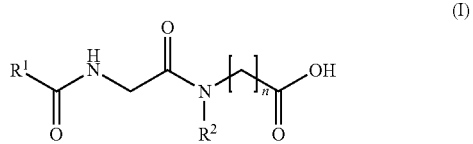
(I)

wherein $R^1$ represents a C1~C4 alkyl group; $R^2$ represents a hydrogen atom or a methyl group; and n represents an integer of 1~6.

In one embodiment, the whitening composition comprises the glycine derivative with addition amount of 0.1~2 wt % (weight ratio) and has a function of inhibiting melanin formation.

According to the invention, although the melanogenesis inhibition mechanism of the glycine derivative is not clear, the experiment proves that the glycine derivative is capable of melanogenesis inhibition. Besides, since the structure of the glycine derivative according to the invention does not comprises an aromatic group, aromatic phenol and derivative thereof, thiol group and derivative thereof, the glycine derivative according to the invention has a derivative structure with oxidative stability. The glycine derivative according to the invention is not easily oxidized while applied in manufacturing a whitening formulation and also has color stability during storage. In addition, the glycine derivative according to the invention has no apparent cytotoxicity and is harmless to human beings. It is convenient to use the glycine derivative according to the invention in manufacturing, applying, and storing a whitening formulation to thereby increase the stability of the formulation. In addition, the glycine derivative according to the invention has optical activity, that is, no enantiomer. The glycine derivative according to the invention has no bioactivity difference due to other existing enantiomer as the impurity and thus all the added amount of the glycine derivative is effective. According to the invention, the glycine derivative is particularly suitable to be applied in a clear aqueous cosmetic caring formulation.

DESCRIPTION OF THE PREFERRED EMBODIMENTS

The above and other objectives, features and advantages of the invention will be further understood from the further technological features disclosed by the embodiments of the invention wherein there are shown and described preferred embodiments of this invention, simply by way of illustration of modes best suited to carry out the invention. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

The present invention is related to a compound as an effective whitening ingredient. According to research of the inventors, it is found that the whitening effect of dipeptides varies. Although there are reports disclosing various dipeptides having whitening effect (for example, Japan patent application No. H05-032533, H06-345797, and H05-170637), since a dipeptide is formed by combining two amino acids comprising one peptide bond, the inventors of the present invention found that the function of inhibiting carbonylation, glycosylation, and oxidation of a dipeptide varies with the structure of the dipeptide. Especially, inhibiting the activity of tyrosinase or polyphenol oxidase cannot be determined only by the peptide bond, that is, practically it is related to the structure of dipeptide or two amino acids comprising the dipeptide. It cannot be determined that dipeptides automatically have the function of inhibiting melanogenesis. For example, carnosine is known as an anti-oxidant but does not have the function of inhibiting melanogenesis.

Furthermore, for example, Girelli et al. (Inhibition of polyphenol oxidases activity by various dipeptides, A. Girelli, E. Mattei, A. Messina, and A. Tarola, J. of Agricultural and Food Chemistry, 2004, 52. 2741-2745) disclose various dipeptides inhibiting polyphenol oxidases activity and the result shows not all dipeptides can inhibit polyphenol oxidases activity. Moreover, for example, the tyrosinase inhibiting rates of dipeptides disclosed in table 1 of Japan patent application No. H05-170637 are in the range of 3%~56%. Therefore, the characteristic of inhibiting the activity of tyrosinase is not determined by the peptide bond but practically depends on the structure of the dipeptide.

One embodiment of the present invention discloses a glycine derivative, having a structure shown in the following general equation (I):

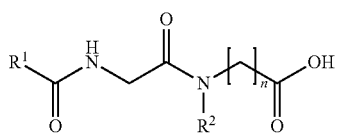

(I)

wherein $R^1$ represents a C1~C4 alkyl group; $R^2$ represents a hydrogen atom or a methyl group; and n represents an integer of 1~6.

In one embodiment, the glycine derivative is 3(2-acetylamino-acetylamino)-propionic acid having a structure shown in the following general equation (II):

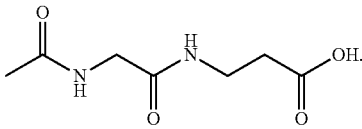

(II)

In one embodiment, the glycine derivative is 4-(2-Acetylamino-acetylamino)-butyric acid having a structure shown in the following general equation (III):

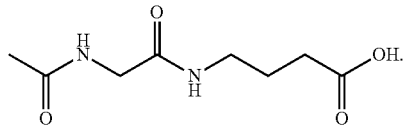

(III)

In one embodiment, the glycine derivative is [(2-Acetylamino-acetyl)-methyl-amino]acetic acid having a structure shown in the following general equation (IV):

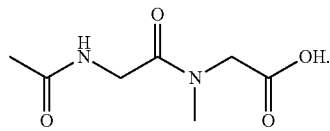

(IV)

In one embodiment, a solution or a buffer solution containing the glycine derivative with addition amount of 0.05~10 wt % (weight ratio) has light transmittance more than or equal to 97% in the wavelength range of 420~500 nm.

In one embodiment, the buffer solution comprises citric acid and salts thereof. The solution or the buffer solution containing the glycine derivative with addition amount of 0.05~10 wt % (weight ratio) has light transmittance more than or equal to 98% at the specific wavelength 440 nm.

Another embodiment of the invention is to provide a whitening composition, comprising: a glycine derivative with addition amount of 0.05∞10 wt % (weight ratio) wherein the glycine derivative has a function of inhibiting melanin formation and has a structure shown in the following general equation (I):

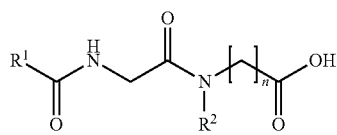

(I)

wherein $R^1$ represents a C1~C4 alkyl group; $R^2$ represents a hydrogen atom or a methyl group; and n represents an integer of 1~6.

In one embodiment, the whitening composition comprises the glycine derivative with addition amount of 0.1~2 wt % (weight ratio) and has a function of inhibiting melanin formation. In one embodiment, the glycine derivative included in the whitening composition can be the examples of the glycine derivative of the present invention, such as 3(2-acetylamino-acetylamino)-propionic acid, 4-(2-Acetylamino-acetylamino)-butyric acid, and [(2-Acetylamino-acetyl)-methyl-amino]-acetic acid.

According to the glycine derivative of the invention, through the cell experiments, it is found that the glycine derivative has the function of inhibiting melanogenesis. While the glycine derivative is applied to skin, it is easily absorbed by skin because of low molecular weight of the glycine derivative of the invention. Besides, the glycine derivative of the invention has no enantiomer, that is, the glycine derivative according to the invention has no bioactivity difference due to other existing enantiomer as the impurity and thus all the added amount of the glycine derivative is effective.

The following further describes the present invention in details through examples. At first, the method for preparing the glycine derivative of the invention is described.

Example 1

Preparation of 3(2-acetylamino-acetylamino)-propionic acid or Acetyl-Glycine-β-Alanine Ac-Gly-OH a (3.77 g, 32.2 mmol) and triethylamine (6.7 mL, 48.1 mmol) were dissolved in 160 mL THF and cooled to −10° C., and isobutylchloroformate (5.02 g, 38.6 mmol) was added. The mixture was stirred at −10° C. for 1 hr. H-beta-Ala-OBzl.PTSA e (11.26 g, 32.0 mmol) and triethylamine (6.7 mL, 48.1 mmol) was dissolved in 160 mL THF, and added into mix anhydride solution. The reaction mixture was stirred at room temperature overnight. The salt was filtrated off and THF was removed in vacuum. The residue obtained was purified by column chromatography using ethyl acetate and heptane as eluent to obtain 5.95 g Ac-Gly-beta-Ala-OBzl f.

Ac-Gly-beta-Ala-OBzl f was dissolved in 200 mL THF, and then added 10% Pd/C. The mixture was stirred under hydrogen. After overnight, the catalyst was removed by filtration and the resulting filtrate was evaporated to 2.49 g white powder g. (yield=41.0%, purity>95%). The compound was characterized by $H^1$ NMR: 1.84, s, 3H; 2.35-2.38, t, 2H; 3.27-3.31, m, 2H; 3.61, d, 2H; 7.85-7.87, t, 1H; 8.03-8.05, t, 1H; 12.22, s, 1H. It is confirmed that it is 3(2-acetylamino-acetylamino)-propionic acid having a structure shown in the above equation (II).

Example 2

Preparation of
4-(2-Acetylamino-acetylamino)-butyric acid) or
Acetyl-Glycine-γ-aminobutyric acid Ac-Gly-OH a (2.52 g, 21.6 mmole) and triethylamine (5 ml, 36.1 mmole) were dissolved in THF (100 ml) and cooled to −10° C., and isobutylchloroformate (3.2 g, 23.8 mmole) was added. The mixture was stirred at −10° C. for 1 hr. H-γAbu-OBzl.PTSA h (7.6 g, 20.8 mmole) and triethylamine (5 ml, 36.1 mmole) was dissolved in THF (90 ml), and added into mix anhydride solution at −5° C. The reaction mixture was stirred at room temperature overnight. The salt was filtrated off and THF was removed in vacuum. The residue was purified by column chromatography using ethyl acetate and heptane as eluent to obtain Ac-Gly-GABA-OBzl i.

The column purified Ac-Gly-γAbu-OBzl i (2.6 g) was dissolved in THF (100 ml), and then added 5% Pd/C (0.26 g). The mixture was stirred under hydrogen. After overnight, the catalyst was removed by filtration and the resulting filtrate was evaporated to white powder j (yield=43.3%, purity>95%). The compound was characterized by $H^1$ NMR: 1.58-1.64, m, 2H; 1.85, s, 3H; 2.19-2.22, t, 2H; 3.04-3.08, m, 2H; 3.61-3.62, d, 2H; 7.81-7.83, t, 1H; 8.02-8.04, t, 1H; 12.04, s, 1H. It is confirmed that it is 4-(2-Acetylamino-acetylamino)-butyric acid having a structure shown in the above equation (III).

Example 3

Preparation of
[(2-Acetylamino-acetyl)-methyl-amino]-acetic acid)
or Acetyl-Glycine-Sarcosine Ac-Gly-OH a (4.10 g, 35.0 mmol), Sar-OBzl.PTSA b (11.71 g, 33.3 mmol), triethylamine (5.58 mL, 40.0 mmol), HOBt (1.35 g, 10 mmol) and DCC (8.25 g, 40.0 mmol) were stirred in 200 mL THF overnight. The mixture was filtered to discard DCU and removed THF in vacuum. The concentrated residue was dissolved in 100 mL ethyl acetate and washed with 100 mL 10% citric acid(aq) twice, 100 mL 5% NaHCO3 (aq) twice and 100 mL brine twice, dried over MgSO4, and evaporated in vacuum to get about 9 g light yellow oily Ac-Gly-Sar-OBzl c.

Ac-Gly-Sar-OBzl was dissolved in 200 mL THF, and then added 10% Pd/C. The mixture was stirred under hydrogen. After overnight, methanol was added to dissolve product. The catalyst was removed by filtration and removed solvent in vacuum. The concentrate residue was recrystallized from THF to obtain 4.49 g white powder d (yield=71.6%, purity>95%). The compound was characterized by $H^1$ NMR: Major: 1.86, s, 3H; 2.99, s, 3H; 3.96, d, 2H; 3.99, s, 2H; 7.94, s, 1H; 12.6-12.9, m, 1H. Minor: 1.85, s, 3H; 2.81, s, 3H; 3.82, d, 2H; 4.10, s, 2H; 7.93, s, 1H; 12.6-12.9, m, 1H. The sample is a mixture of rotational isomers. It is confirmed that it is [(2-Acetylamino-acetyl)-methyl-amino]-acetic acid having a structure shown in the above equation (IV).

The following performs various tests on the compounds (II), (III), or (IV).

Melanogenesis Inhibition Test

In the melanogenesis inhibition test, Kojic acid is used as the positive control. Compounds (II), (III), and (IV) and ascorbic acid derivative are evaluated regarding their whitening effect under a concentration of no cytotoxicity to test the melanogenesis inhibiting ability.

The cytotoxicity test is evaluated by MTT assay. The compounds for evaluating whitening effect has $LD_{50}$ (half maximal lethal dose) of 5000 mg/Kg to 3T3 (Swiss albino mouse fibroblast) and B16-F10 (Mus musculus skin melanoma) cells and the safety of using the compounds (II), (III), and (IV) is the same as that of ascorbic acid derivative that is known to be no apparent cytotoxicity and harmless to human beings.

B16-F10 B16-F10 cells are placed in a 96-well plate and each well comprises 5000 cells (5000 cells/well). The cells are incubated at 37° C. in 5% $CO_2$ and 10% FBS DMEM (Fetal Bovine Serum Dulbecco's modified Eagle's medium) overnight to allow the cells to attach to the wells.

Melanin production rate (%) is defined by the following equation:

$$\text{Melanin production rate (\%)} = \left(\frac{OD_T - OD_B}{OD_N - OD_B}\right) \times 100\%$$

where $OD_T$ represents the optical density of the test sample at the wavelength 405 nm by the spectrophotometer; $OD_B$ represents the optical density of the blank control at 405 nm; $OD_N$ represents the optical density of the negative control at 405 nm. The negative control comprises 0.1 mg/ml of tyrosine and 1 μM of α-MSH (α-melanocyte stimulating hormone). The blank control comprises 0.1 mg/ml of tyrosine but no α-MSH. The test sample is prepared by stocking 5 wt % of compound (II), (III), or (IV) in phenol red free DMEM and 5 wt % FBS no phenol red DMEM with 0.1 mg/ml tyrosine and 1 μM α-MSH is prepared and filtered by a 0.22 μm filter. 0.1 mg/ml tyrosine may cause the medium over saturated and thus centrifugal filtration is required. The testing sample was prepared in the medium mentioned above.

Until cells were at full confluence, they were treated with test samples and reference samples (prepared above) 100 μL each well for 3 days. After 3 days incubation, 100 μL 1N NaOH is added in each well. The solution is placed on a shaking table at least 10 minutes. The optical density of the test sample at 405 nm is measured.

The positive control is Kojic acid (500 ppm concentration). Based on student's t-test, the P value is less than 0.05. The test result is shown in table I.

TABLE I

| | Sample concentration | |
|---|---|---|
| | 0.2% | 0.4% |
| | melanin production rate % ± standard deviation | |
| ascorbic acid 2-glucoside (AA2G) | 86.8 ± 3.4 | 76.2 ± 10.5 |
| ethyl ascorbic acid | 86.4 ± 2.6 | 78.9 ± 6.3 |
| ascorbic acid 2-phosphate magnesium | 105.3 ± 3.4 | 88.4 ± 11.4 |
| carnosine | 129 ± 1.7 | 141 ± 10.5 |
| Compound(II) | 64.7 ± 12.8 | 11.0 ± 2.9 |
| Compound(III) | 70.4 ± 10.0 | 14.2 ± 3.0 |
| Compound(IV) | 60.8 ± 22.3 | 15.0 ± 5.6 |

Kojic acid (positive control; 500 ppm): melanin production rate(%) = 33%

Color Stability Test

The test samples (compounds (II), (III), and (IV)) and the reference sample are separately dissolved in water and a buffer solution with pH=6 to prepare 0.5 wt % solutions. The buffer solution with pH=6 is a mixture solution of 3.8 ml 0.1M citric acid and 16.2 ml citrate. 25 mg of a test sample are dissolved in the mixture solution to prepare a 0.5 wt % solution. Then, the solutions are placed in a 45° C. oven to perform an accelerated color stability test. After 14 and 28 days, the spectrophotometer is used to measure the light transmittance of these solutions at 440 nm. After 28 days, the solutions are analyzed by HPLC/DAD(diode array detection) to measured the absorption in the wavelength of 400~500 nm and the results show no absorption signal. Table II shows the results of the test samples dissolved in water and Table III shows the results of the test samples dissolved in the pH=6 buffer solution.

TABLE II

| | Duration | |
|---|---|---|
| | 14 days | 28 days |
| | Test solution | |
| | Aqueous solution | |
| Test sample | Transmittance % (440 nm) | |
| Compound (II) | 98.9 | 99.8 |
| Compound (III) | 99.6 | 99.5 |
| Compound (IV) | 99.7 | 100 |
| Kojic acid | 94.9 | 81 |
| arbutin | 96.7 | 95.4 |
| AA2G | 97.8 | 96.9 |
| Ascorbic acid | 37.8 | 20.8 |

TABLE III

| | Duration | |
|---|---|---|
| | 14 days | 28 days |
| | Test solution (pH = 6) | |
| | Citric acid buffer solution | |
| Test sample | Transmittance % (440 nm) | |
| Compound (II) | 99.4 | 99.3 |
| Compound (III) | 100 | 99.9 |
| Compound (IV) | 100 | 100 |
| Kojic acid | 34.8 | 4.0 |
| Ethyl ascorbic acid | 98.6 | 97.5 |
| Magnesium ascorbic acid-2-phosphate | 85.6 | 80.9 |
| Ascorbic acid | 0.7 | 2.1 |

The following uses the embodiments of formulations to illustrate the applications of the compounds according to the invention but the invention is not limited these embodiments.

The first formulation embodiment is an example of preparing a moisturizing toning lotion.

| Group | Name | % |
|---|---|---|
| A | Glyceryl Polymethacrylate (and) Propylene Glycol | 1.20 |
| A | Glyceryl Polymethacrylate (and) Propylene Glycol (and) PVM/MA Copolymer | 11.40 |
| A | PVM/MA Decadiene Crosspolymer | 0.25 |
| A | water | To 100.00 |
| B | Sclerotium Gum | 3.90 |
| B | Sodium Hyaluronate | 7.70 |
| B | Compound (III) | 0.20 |
| B | Glycerin | 3.80 |
| B | Hydrolyzed *Lepidium Meyenii* Root | 3.80 |
| B | Methylisothiazolinone | 0.10 |
| C | Octoxynol-11 (and) Polysorbate 20 | 0.30 |
| C | Fragrance | 0.10 |

The blending method can use any well-known method. For example, the components in group A are blended together until becoming uniform and then the components in group B are added separately. After stirring, the pre-blended components in group C are added into the mixture of groups A and B and blended together until becoming uniform.

The second formulation embodiment is an example of preparing a whitening serum.

| Group | Name | % |
|---|---|---|
| A | Water | To 100.00 |
| A | Hydroxyethylcellulose | 30.00 |
| A | PVM/MA Decadiene Crosspolymer | 13.00 |
| B | Compound (II) | 1.00 |
| B | Propylene Glycol (and) Water (and) *Chamomilla Recutita* (*Matricaria*) Flower Extract | 2.00 |
| B | Methylisothiazolinone | 0.10 |
| C | Water | 3.00 |
| C | Scleroglucan Gum | 2.00 |
| D | Octoxynol-11 (and) Polysorbate 20 | 0.15 |
| D | Fragrance/Perfume | 0.10 |

The blending method can use any well-known method. For example, the components in group A are blended together until becoming uniform and then the components in group B are added separately. After stirring, the pre-blended components in groups C and D are added into the mixture of groups A and B and blended together until becoming uniform.

The third formulation embodiment is an example of preparing a skin rejuvenation lotion.

| Group | Name | % |
|---|---|---|
| A | Cetyl Alcohol (and) Glyceryl Stearate (and) PEG-75 Stearate (and) Ceteth-20 (and) Steareth-20 | 4.00 |
| A | Myristyl Myristate | 2.00 |
| A | Dioctyl Sebacate | 4.00 |
| A | Ethylhexyl Isononanoate | 3.00 |
| A | *Macadamia Integrifolia* Nut Oil | 5.00 |
| B | Water | To 100.00 |
| B | Carbomer (2%) | 15.00 |
| | Sodium Hydroxide(10%) | 0.80 |
| C | Compound (III) | 1.00 |
| C | Sodium Hyaluronate(1%) | 2.00 |
| C | Methylisothiazolinone | 0.10 |
| C | Fragrance | 0.05 |

The blending method can use any well-known method. For example, the components in groups A and B are separately heated to 80° C. and stirred until becoming uniform. Then, the mixture of the components in group B is added into the mixture of the components in group A. After stirring 5 min and cooling, NaOH is added to neutralize the mixture. After the temperature is cooled to 45° C., the components in group C are added one by one and stirred until becoming uniform.

In conclusion, the glycine derivative according to the invention can be used as an effective ingredient for inhibiting melanogenesis and can be applied in various skin care products and cosmetics by a form of cream, lotion, gel, toning lotion, etc. as a whitening ingredient. The whitening effect of the glycine derivative according to the invention is confirmed experimentally. Besides, since the structure of the glycine derivative according to the invention does not comprises an aromatic group, aromatic phenol and derivative thereof, thiol group and derivative thereof, the glycine derivative according to the invention has a derivative structure with oxidative stability. The glycine derivative according to the invention is not easily oxidized while applied in manufacturing a whitening formulation and the glycine derivative also has color stability during storage. In addition, the glycine derivative according to the invention has no apparent cytotoxicity and is harmless to human beings. In addition, the glycine derivative according to the invention has optical activity, that is, no enantiomer. The glycine derivative according to the invention has no bioactivity difference due to other existing enantiomer as the impurity and thus all the added amount of the glycine derivative is effective. It is convenient to use the glycine derivative according to the invention in manufacturing, applying, and storing a whitening formulation to thereby increase the stability of the formulation because of excellent stability. The glycine derivative is particularly suitable to be applied in a clear aqueous cosmetic caring formulation.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for inhibiting melanin formation, comprising: topically applying a skin whitening composition to skin of a human, wherein said skin whitening composition comprising an effective amount of glycine derivative having a structure represented in the following general equation (I):

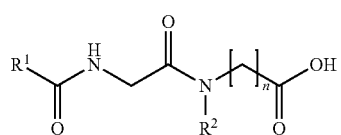

(I)

wherein $R^1$ represents a C1~C4 alkyl group; $R^2$ represents a hydrogen atom; and n represents an integer of 2 or 3.

2. The method for inhibiting melanin formation according to claim 1, wherein the glycine derivative is 3(2-acetylamino-acetylamino)-propionic acid having a structure shown in the following equation (II):

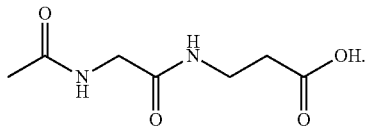

(II)

3. The method for inhibiting melanin formation according to claim 1, wherein the glycine derivative is 4-(2-Acetylamino-acetylamino)-butyric acid having a structure shown in the following equation (III):

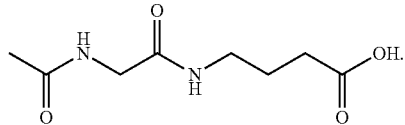

(III)

4. A method for inhibiting melanin formation, comprising:
topically applying a skin whitening composition to skin of a human, wherein said skin whitening composition comprising a free acid form of a glycine derivative with addition amount of 0.05~10 wt % (weight ratio) wherein the free acid form of the glycine derivative has a function of inhibiting melanin formation and has a structure shown in the following general equation (I):

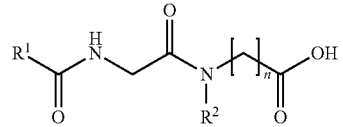

(I)

wherein $R^1$ represents a C1~C4 alkyl group; $R^2$ represents a hydrogen atom; and n represents an integer of 2 or 3.

5. The method for inhibiting melanin formation according to claim 4, wherein the composition comprises the free acid form of the glycine derivative with addition amount of 0.1~2 wt % (weight ratio) and has a function of inhibiting melanin formation.

6. The method for inhibiting melanin formation composition according to claim 4, wherein the free acid form of the glycine derivative is 3(2-acetylamino-acetylamino)-propionic acid having a structure shown in the following general equation (II):

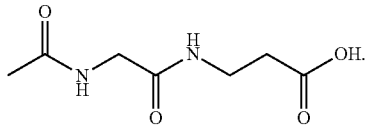

(II)

7. The method for inhibiting melanin formation composition according to claim 4, wherein the free acid form of the glycine derivative is 4-(2-Acetylamino-acetylamino)-butyric acid having a structure shown in the following general equation (III):
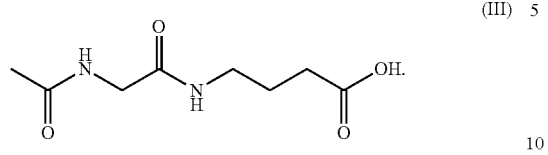
(III)